(12) United States Patent
Pedicini et al.

(10) Patent No.: US 12,329,585 B2
(45) Date of Patent: Jun. 17, 2025

(54) ROTARY TOOL WITH REDUCED RECOIL FOR ORTHOPEDIC SURGERY

(71) Applicant: Fidelis Partners, LLC, Cheyenne, WY (US)

(72) Inventors: Christopher Pedicini, Brentwood, TN (US); Joshua Pedicini, Nashville, TN (US)

(73) Assignee: FIDELIS PARTNERS, LLC, Cheyenne, WY (US)

( * ) Notice: Subject to any disclaimer, the term of this patent is extended or adjusted under 35 U.S.C. 154(b) by 472 days.

(21) Appl. No.: 17/845,055

(22) Filed: Jun. 21, 2022

(65) Prior Publication Data

US 2022/0313382 A1    Oct. 6, 2022

Related U.S. Application Data

(63) Continuation-in-part of application No. 17/584,349, filed on Jan. 25, 2022, now Pat. No. 11,877,780.
(Continued)

(51) Int. Cl.
*A61B 90/00*        (2016.01)
*A61B 17/16*        (2006.01)
(Continued)

(52) U.S. Cl.
CPC .......... *A61B 90/03* (2016.02); *A61B 17/1626* (2013.01); *A61B 17/1628* (2013.01); *A61B 17/1631* (2013.01); *A61B 17/92* (2013.01); *A61B 2017/00123* (2013.01); *A61B 2090/031* (2016.02); *A61B 2090/066* (2016.02)

(58) Field of Classification Search
CPC .......... A61B 17/92; A61B 90/03; A61B 90/02
See application file for complete search history.

(56) References Cited

U.S. PATENT DOCUMENTS

| 7,402,040 B2 | 7/2008 | Turri | |
| 2008/0210451 A1* | 9/2008 | Aoki | B25D 17/24 173/162.1 |

(Continued)

FOREIGN PATENT DOCUMENTS

JP    2019-528089 A    10/2019

OTHER PUBLICATIONS

Extended European Search Report issued Dec. 2, 2024 in corresponding European Patent Application No. 1 22746488.0, 11 pages.
(Continued)

*Primary Examiner* — Christian A Sevilla
(74) *Attorney, Agent, or Firm* — XSENSUS LLP

(57) ABSTRACT

A rotary torque releaseor for orthopedic surgery includes an output anvil and a hammer that is capable of imparting linear and rotary force on the anvil. The anvil may be moveable on a leadscrew element to alternately generate energy in an energy storage means and to move along the leadscrew element to torque release the anvil. A viscoelastic mechanism or a dampening mechanism is used to reduce the reflected force and or torque during operation of the rotary torque releaseor. High frequency axial movements by the torque releaseor obviate the need for a surgeon to provide an external push force on the torque releaseor in order to perform a successful surgical operation.

20 Claims, 11 Drawing Sheets

Related U.S. Application Data

(60) Provisional application No. 63/277,754, filed on Nov. 10, 2021, provisional application No. 63/188,542, filed on May 14, 2021, provisional application No. 63/141,786, filed on Jan. 26, 2021.

(51) Int. Cl.
*A61B 17/92* (2006.01)
*A61B 17/00* (2006.01)

(56) References Cited

U.S. PATENT DOCUMENTS

| | | |
|---|---|---|
| 2010/0268235 A1 | 10/2010 | Teichmann |
| 2012/0232562 A1* | 9/2012 | Mani ................... A61F 2/4612 606/100 |
| 2015/0182351 A1* | 7/2015 | Behzadi ................ A61B 17/92 606/91 |
| 2018/0055552 A1* | 3/2018 | Pedicini ............... A61B 17/92 |
| 2019/0216521 A1* | 7/2019 | Chhatrala ........... A61B 17/921 |

OTHER PUBLICATIONS

Japanese Office Action issued Mar. 11, 2025 in corresponding Japanese Patent Application No. 2023-545234, 27 pages.

\* cited by examiner

ROTARY TOOL WITH REDUCED RECOIL FOR ORTHOPEDIC SURGERY

CROSS-REFERENCE TO RELATED APPLICATIONS

The present application is a non-provisional application which is a continuation in part of U.S. patent application Ser. No. 17/584,349 filed Jan. 25, 2022, which claims priority under 35 U.S.C. § 119 on U.S. Provisional Patent Application Ser. No. 63/141,786, filed on Jan. 26, 2021, on U.S. Provisional Patent Application Ser. No. 63/188,542, filed on May 14, 2021, and on U.S. Provisional Patent Application Ser. No. 63/277,754, filed on Nov. 10, 2021, the disclosures of which are incorporated by reference herein.

FIELD OF THE DISCLOSURE

The present disclosure relates to a rotary reamer for use by surgeons and/or surgical robots, and more particularly, to a rotary reamer in which negligible reactionary force is imparted to the surgeon and/or robot.

BACKGROUND OF THE DISCLOSURE

The current direction of surgery is towards using robot assistance in the surgery process. In this regard, an end effector of the robot may be used by a robot, for example, to perform a surgical procedure. The end effector is a device, tool, or manipulator at an end of the robot that is capable of engaging and interacting with a surgical site. The end effector is directed by the robot to perform surgical actions. In the field of robotic surgery, the end effector may comprise a surgical tool.

To date, robotic automation in surgery has worked well in laparoscopic procedures and surgeries with low energy requirements, however, in the orthopedic environment where large forces and energies are routine, the adoption of the robot has been hindered. In such an environment and in the field of orthopedic surgery, larger energy requirements have necessitated a different approach (such as machining) due to the inability of surgical robots to handle the magnitude of reactionary forces that result from typical large bone surgical tools (such as saws, drills or reamers).

An exemplary robot that is used in large bone surgeries is Stryker Corporation's MAKO product. The MAKO has three purposes: enhanced planning, dynamic joint balancing, and robotic-arm assisted bone preparation.

As part of its operation, the robot must have the bone geometry of the surgical site identified in order to accurately navigate, guide, and manipulate its end effector through the surgical site. Such identification of bone geometry is referred to as registration. Existing surgical power tools produce a significant amount of reactionary torque in the case of a surgical reamer when used in orthopedic surgery. This torque and or shock can not only cause the robot to lose its registration but it can also damage the robot's highly intricate machinery and components.

Rotary reamers are used in hip and shoulder replacement surgery such as when preparing the cavity for the acetabular cup of a prosthetic hip. These rotary tools have a significant reactionary torque associated with the surgical procedure. This can result in the tool being wrenched from the grip of the surgeon performing the operation and in severe cases damage to the surgeons wrist or forearm. Clearly, such reactionary torque can cause navigational or guidance errors which in the case of use by a robot will often result in loss of registration and shut down of the robot. Testing has shown this to be the case and is one of the most common complaints about using robots for large bone orthopedic surgery.

The navigation capability is arguably the most important feature of orthopedic robotics. For a successful surgery, the robot must hold the tool (or instrument) in the correct orientation and alignment with respect to the bone. If the surgical instrument is allowed to move off the stereotactic boundary, then the surgery can suffer from any of a number of drawbacks, including injury to soft tissue if the instrument is still powered. Currently available rotary tools can generate large destabilizing forces (e.g., reactionary torque caused by the reamer encountering and/or snagging on a hard section of bone.). These forces interfere with a robots programmed navigation and can result in the robot shutting down.

Furthermore, there are at least two problems with simply placing a surgical power tool designed for a surgeon onto a robot. One, the reactionary force/torque imparted by the tool can move the robot off of its guided path. Secondly in large bone surgery, the robot often cannot supply sufficient linear force to enable progression of the reamer into the acetabulum. The surgeon often has to exert linear force on the tool in order to achieve the desired outcome.

Accordingly, a need exists for a tool that allows for easier operation by the surgeon as well as creating a pathway to robotic and eventually full autonomous surgery.

SUMMARY OF THE DISCLOSURE

The present disclosure provides for a rotary and/or rotary/linear surgical tool which through the use of output coupling and decoupling significantly reduces the reflected torque while achieving a similar outcome as current rotary surgical reamers. Furthermore, in the case that axial force supplementation is used, both the linear and rotary force requirements are significantly reduced as compared to conventional surgical reamers and drills. For example, current art requires the surgeon to apply all the required linear force to advance the surgical reamer into the surgical site. This linear force can be in excess of 25 pounds, which is far more than a surgical robot is capable of providing. It has been discovered that axial force supplementation by the disclosed tool reduces the required linear supporting force from the surgeon by ~50%.

In view of the disadvantages of currently available rotary tools as described herein, the purpose of the present disclosure is to provide a solution to the high reactionary forces that occur from the use of orthopedic surgical tools. These solutions work to reduce the reactionary forces upon a surgical robot and/or the surgeon to allow better control of the surgical instrument (for example, positioning thereof) during surgery. In addition to reducing the reactionary forces, it is also the purpose of this disclosure to mechanically provide all or a significant portion of the required forces to complete the surgery such that the surgeon and/or robot should only have to guide the tool with minimal force. It is understood that all references to rotary tools, reaming tools, etc. within this application are intended only to cover orthopedic tools.

In an embodiment, the tool comprises a method by which the torque being delivered to the surgical implement is sensed and, when a threshold torque value is reached or exceeded, the input torque may decouple from the output torque temporarily and then recouple with an increased rotary torque to the surgical implement. Said threshold torque value is preferably a torque lower than the torque which could damage the operating robot or surgeon's wrist.

It has been discovered that the transition point or threshold torque should occur at less than 45 inch pounds and more preferably less than 35 inch pounds. It is to be understood that "surgical tool" refers to the invention disclosed herein, while "surgical implement" refers to attachments to the surgical tool's output. For example, surgical tool may refer to the handpiece while surgical implement may refer to a semi-hemispherical reamer that attaches to the surgical tool output In an embodiment, a tool comprises a hammer, an output anvil, and an energy storage component (which may comprise, in an embodiment, a spring). The hammer and anvil are operatively coupled to and are capable of being rotated by a lead screw element (an example of such being a Torqspline®). Upon rotation, when a sufficient load on the output anvil is reached, the output anvil and hammer may temporarily cease being rotated by the lead screw element, the hammer may translate up the lead screw element to energize the energy storage component until the hammer and output anvil are so aligned to allow the now-energized energy storage component to act on the hammer to allow the hammer to translate down the lead screw element (while also rotating) to increase the output torque without a corresponding change to the reactionary torque.

The minimal reactionary torque is a result of two things: first, substantially decoupling the hammer from the output anvil at the threshold torque. This restricts the reactionary torque to a certain threshold value. During this period, the motor continues to rotate but instead of turning the output anvil, energy is stored in the energy storage component. Upon sufficient time, energy storage, or rotation of the hammer, the hammer recouples to the output anvil imparting a short but sudden spike in the rotational torque to the anvil and surgical implement. This allows, for example, the reamer to overcome a high load area (such as sclerotic bone/bone spurs in the acetabulum), with minimal reactionary torque to the surgeon. The high torque is generated as a result of the extra energy from the energy storage component being imparted on the hammer before its subsequent re-coupling to the anvil and surgical implement.

The translation and rotation of the hammer in the above-mentioned mechanism could be partitioned in such a way as to impart rotary motion and linear/axial movement simultaneously. It has been discovered that adding an axial movement element to the reaming process increases the overall speed of the reaming stage while also reducing surgeon fatigue (the surgeon does not need to apply the linear push force that they do with a normal reamer. This push force can be in excess of 50 pounds and is often 20 pounds or more).

In another embodiment, a rotary axial reaming tool (also referred to herein as reaming tool, rotary tool, rotary reamer, torque releasing tool, torque decoupling tool) comprises a hammer, an output anvil, and an energy storage component (which component may comprise, in an embodiment, at least one spring, and, in a further embodiment, an additional spring to enable an axial movement). The hammer and anvil are operatively coupled to and are capable of being rotated by a lead screw element. When the user pushes the output anvil into a bone surface, the anvil will also compress a linear actuator spring. The linear actuator spring selectively engages variable axial force supplementation which force supplementation inherently enables axial movement. Axial force supplementation is defined as force(s) supplied by the tool in the axial direction which supplement the surgeons linear push force. This axial force supplementation embodiment can be combined with a reactionary torque releasing embodiment as mentioned earlier and further described herein.

DESCRIPTION OF THE DRAWINGS

The advantages and features of the present disclosure will become better understood with reference to the following detailed description and claims taken in conjunction with the accompanying drawings, wherein like elements are identified with like symbols, in which:

FIG. 73 shows a cross section view of a rotary axial reaming tool wherein the linear actuator spring is compressed.

DETAILED DESCRIPTION OF THE DISCLOSURE

Figure 1:
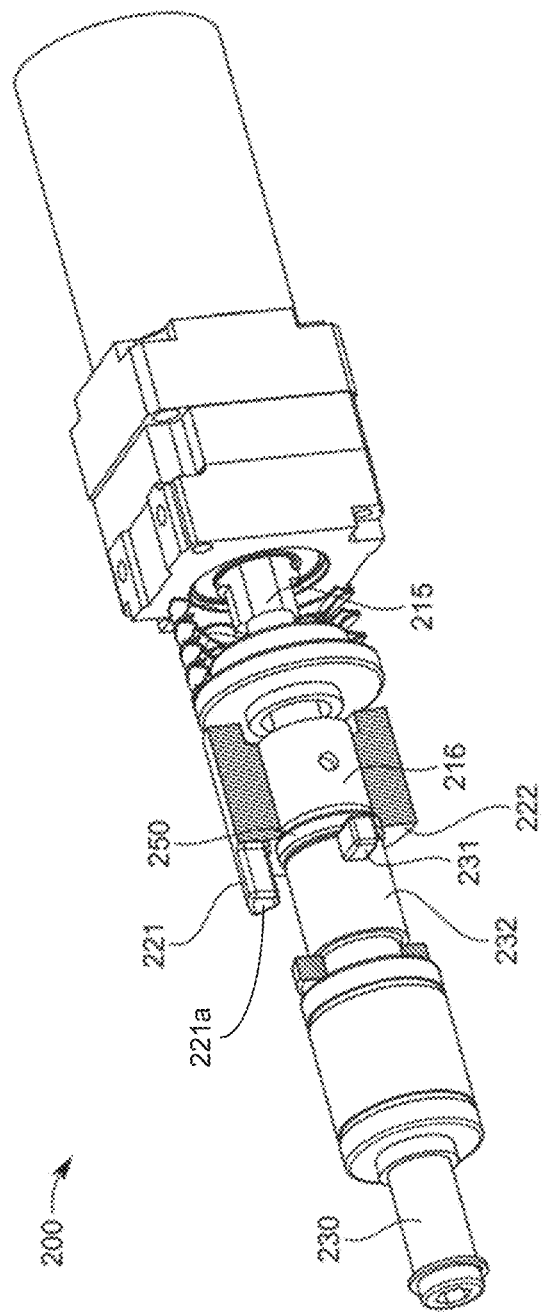
FIG. 1 shows a cutaway view of a rotary torque releasing tool, in accordance with an exemplary embodiment of the present disclosure.

The exemplary embodiments described herein detail for illustrative purposes are subject to many variations in structure and design. It should be emphasized, however, that the present disclosure is not limited to a particular surgical tool and/or robotic end effector as shown and described. That is, it is understood that various omissions and substitutions of equivalents are contemplated as circumstances may suggest or render expedient, but these are intended to cover the application or implementation without departing from the spirit or scope of the claims of the present disclosure. The terms "first," "second," and the like, herein do not denote any order, quantity, or importance, but rather are used to distinguish one element from another, and the terms "a" and "an" herein do not denote a limitation of quantity, but rather denote the presence of at least one of the referenced item.

The present disclosure provides for rotary surgical tools for orthopedic surgery and more specifically to those tools designed to minimize reactionary forces during large bone orthopedic surgery. As used herein, the tool may also be referred to as a reaming tool, rotary tool, rotary reamer, rotary axial surgical tool, rotary axial reamer, rotary torque releasing tool, or torque decoupling tool. A rotary torque releasing tool in this context may be understood to be a tool which effects rotary motion to a surgical implement and can further decouple the operator of the tool from the output torque when a certain threshold torque value is reached. Torque that is felt by the operator of the tool is defined in this context as "reactionary torque." For example, the user will not feel a reactionary torque at or above a certain threshold torque value which can be set to be less than 45 inch-pounds (in-lbs) and more preferably less than 35 in-lbs.

It is necessary to define certain events as they will be referenced throughout and are common to most embodiments of the present disclosure. The drivetrain is an electric motor with an optional gear reducer. A decoupling event is any event in which the rotational revolutions per minute (rpm) of the drivetrain operates at at least 15% higher rpm than the output anvil. In this disclosure, decoupling events occur when threshold torque values are reached and/or exceeded. Threshold torque values are defined in this disclosure to be less than 45 in-lbs and more preferably less than 35 in-lbs. Decoupling events are necessarily followed by a recoupling event. A recoupling event, is defined herein as an event in which the rotational rpm of the drivetrain operates within a 10% window of the output anvil rpm. Recoupling events result in an increase in output torque of at least 50% of the threshold torque. An axial contact event as contemplated by this disclosure is any event in which an axial force is imparted on an output anvil and by association, a surgical implement.

In a still further embodiment, the tool comprises one or more sensors which establish spatial location of the output anvil with respect to the patient. In a still further embodiment, the measurements that determine spatial location are coordinated with the operation of the tool In an embodiment, the tool is designed in such a fashion as to isolate the tool function from the recoil or reactionary force by using a "free flight torque releasing member". The free flight (or thrown) member, as used herein, is a moving member of and within the tool, a portion of which movement is in free flight with respect to the tool. The torque release of the thrown member onto a receiving member imparts a consistent force onto the surgical implement of the tool but equally important is the fact the launching of the thrown member is a predictable impulse which can be compensated for by a sleeve, slide cage or the like. In an embodiment, the reactionary force that is seen at the gripping surface is reduced by extending the time period over which the thrown member torque releases a surface. This is accomplished through conservation of momentum $(m_1 v_1 = m_2 v_2)$, which can also be written in terms of impulse as $F_1 \Delta t_1 = F_2 \Delta t_2$ (where F is force and $\Delta t$ is the time period over which that force occurs). Although the equation is for linear momentum, this concept applies to rotational momentum as well.

Figure 4:
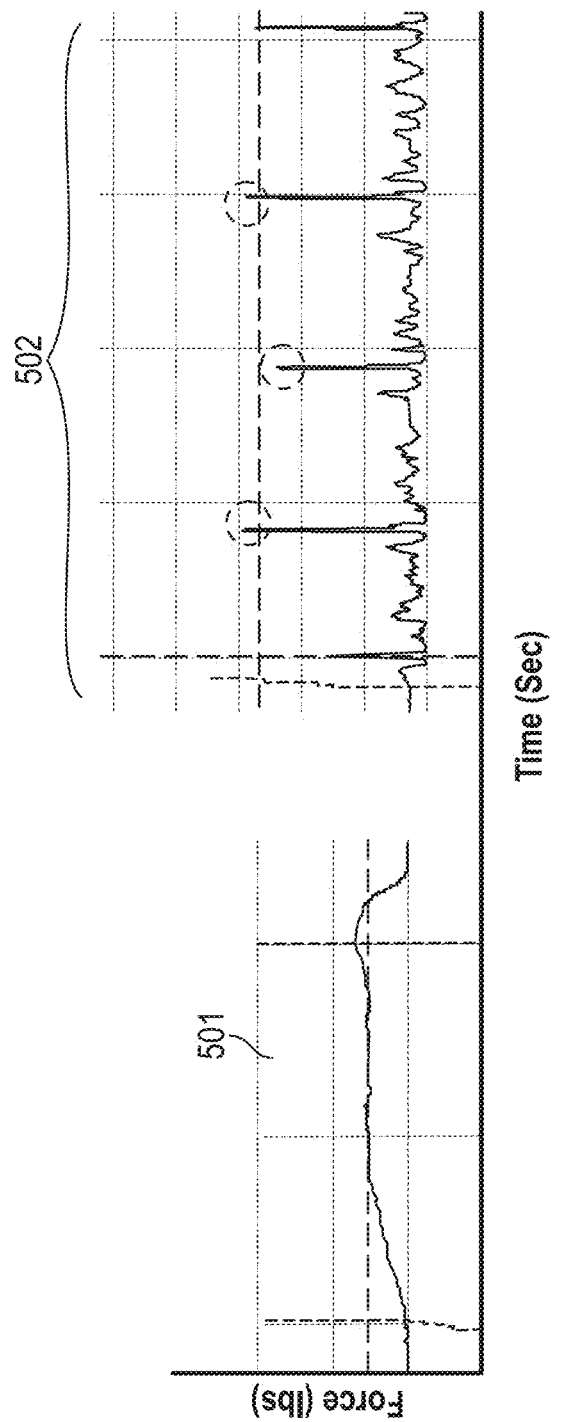
FIG. 4 shows a comparison of the support force applied to the back of a typical surgical reamer and the linear force imparted by an exemplary embodiment of a rotary axial reaming tool according to one or more aspects of the disclosed subject matter.
Figure 5A:
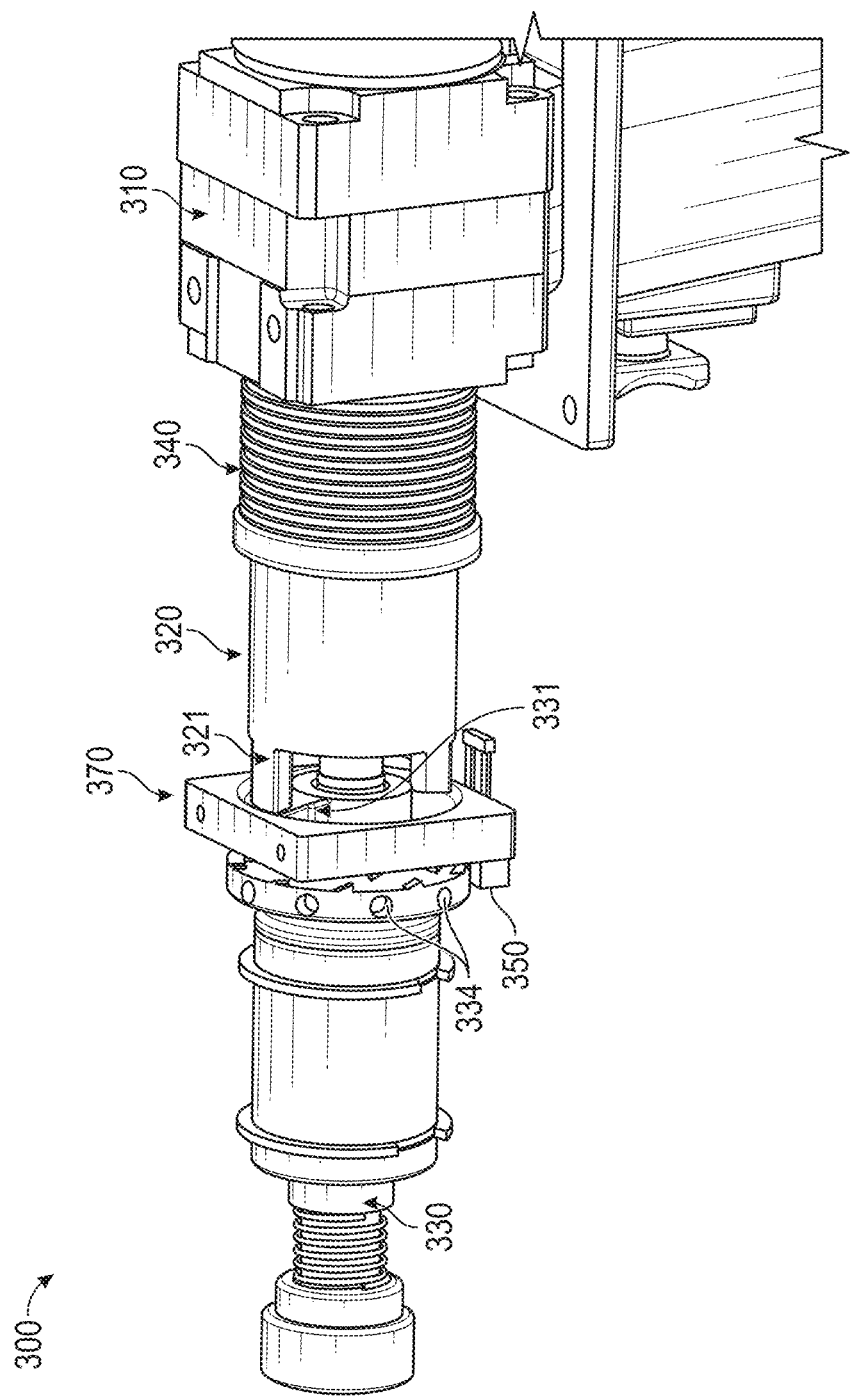
FIG. 5A shows an internal view of a rotary reaming tool with an optional axial displacement in accordance with an exemplary embodiment of the present disclosure.
Figure 5B:
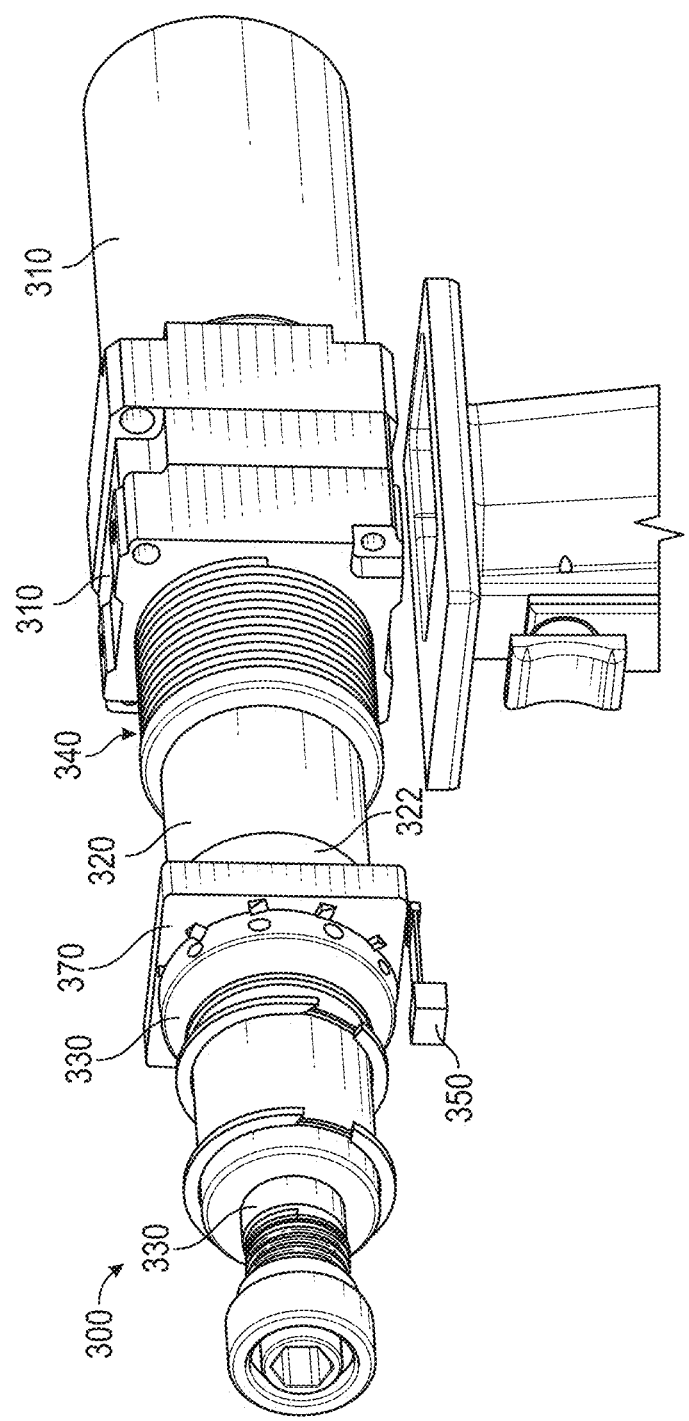
FIG. 5B shows an internal view of a rotary reaming tool with an optional axial displacement in accordance with an exemplary embodiment of the present disclosure.
Figure 5C:
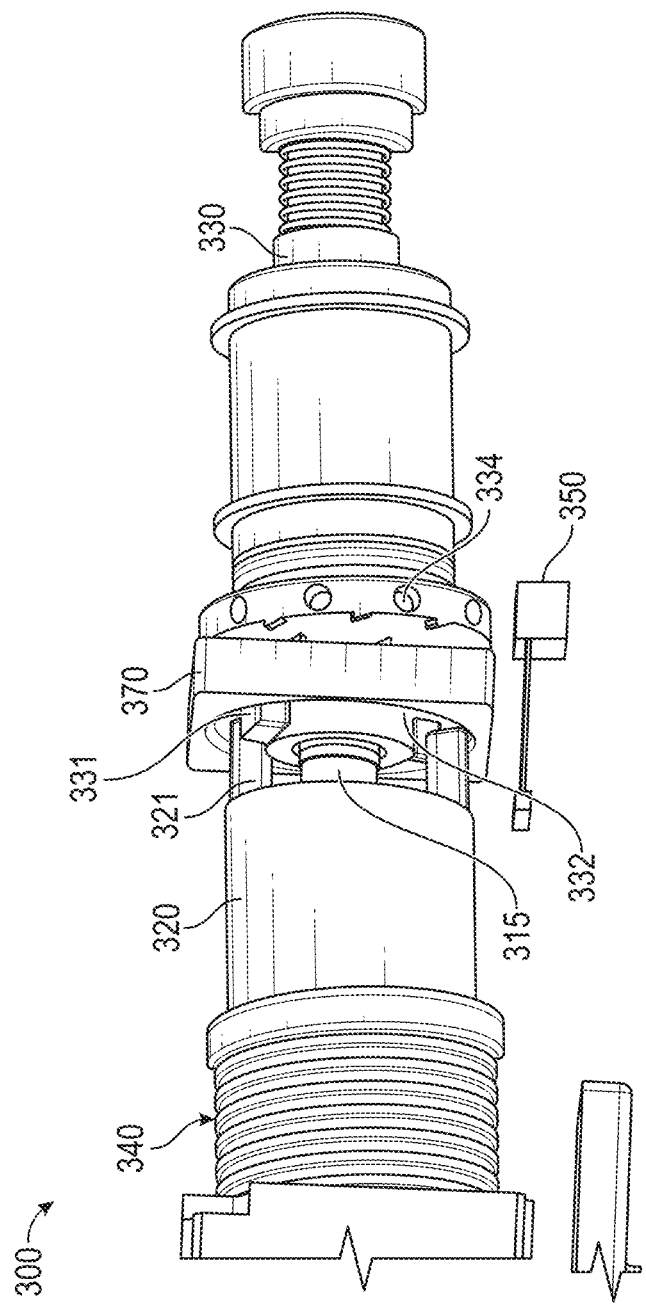
FIG. 5C shows an internal view of a rotary reaming tool with an optional axial displacement in accordance with an exemplary embodiment of the present disclosure.
Figure 8:
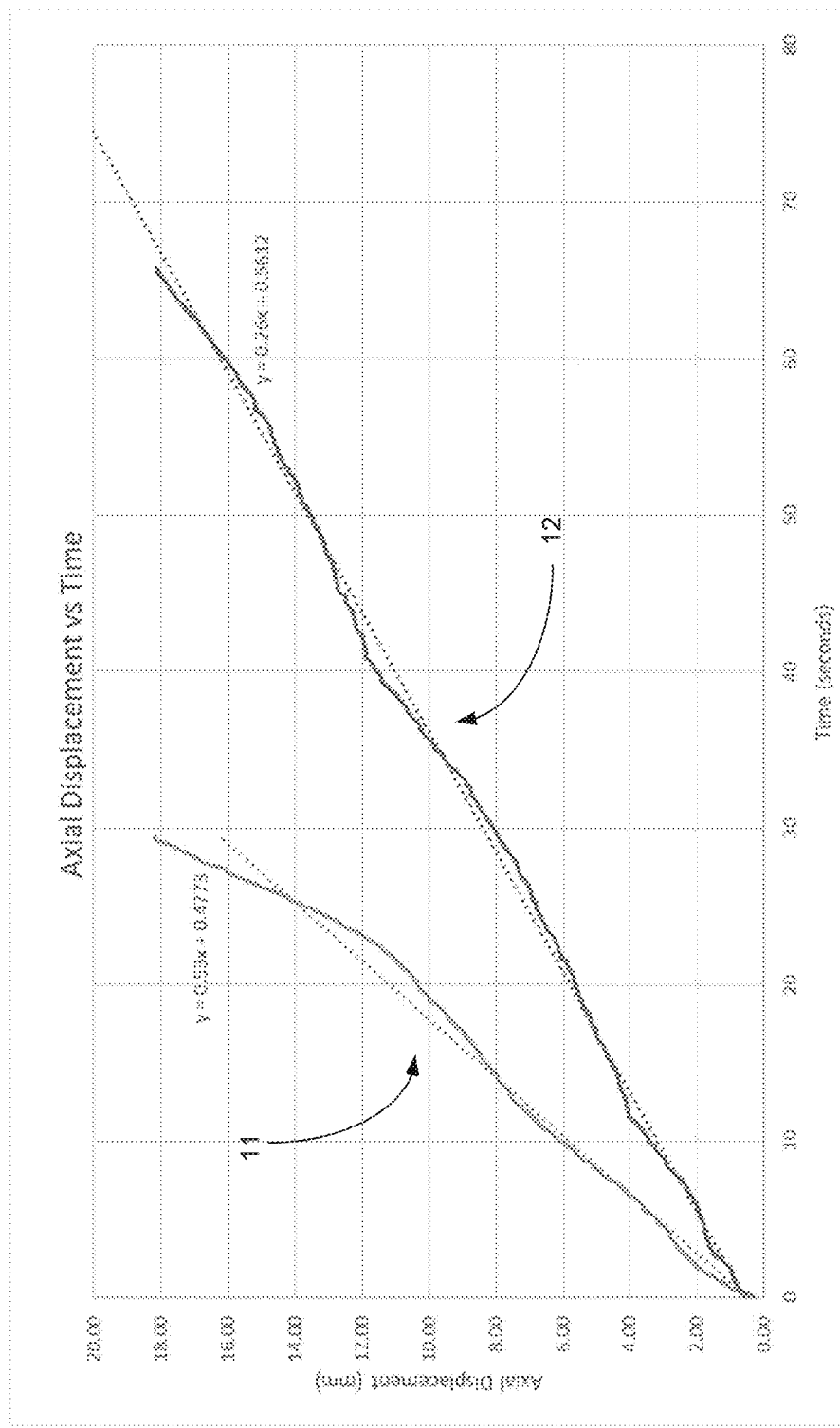
FIG. 8 shows a graph of axial displacement versus time for a reamer tool with axial force supplementation compared to a reamer tool without axial force supplementation.

In another embodiment, rotational action can be combined with an axial movement. Axial movements as contemplated by this disclosure comprise a throw that is less than 2 mm per axial contact event and more preferably less than 1.5 mm per axial contact event. An axial contact event as contemplated by this disclosure is any event in which an axial force is imparted on the output anvil and by association, a surgical implement. It was unexpectedly discovered that adding a small (less than 1 mm) axial displacement reduced the linear force necessary on the tool by over 50% in the initial reaming of the acetabulum. Referring to FIG. 4, curve 501 shows a typical axial force supplied by the tool operator onto a conventional surgical reamer. Curve 502 shows an axial force supplementation mechanism which results in axial movement. The peaks that are circled represent axial contact events, wherein the axial contact events supply the axial force required for axial movement. Referring to FIG. 8, it is clear that a small axial movement significantly decreases the reaming process duration. The curve was created by measuring the rate of progression of a semi-hemispherical reamer cup (surgical implement) being driven by a constant force (12.5 lbs) into a bone-like analogue. Curve 12 shows axial displacement vs time for a typical surgical reamer tool. Curve 11 shows axial displacement vs time for an exemplary embodiment of the present disclosure in which the rotational action of the tool is combined with an axial movement.

In an embodiment, the tool has the capability to determine the stiffness of the surgical site by measuring the rotational displacement per recoupling event with a sensor 350. A recoupling event results in a predictable amount of rotational torque to the output anvil. As a result, the tool of the present disclosure can be configured to indicate a "stalling" condition. For example, the tool might count 10 recoupling events and determine that the reamer has only moved by 0.1 degree rotationally over that period of time. The tool may thereupon indicate to the surgeon/robot (e.g., through a status light, sound or a pause or slowing of the tool's operation) that the reamer is no longer advancing and a decision could be made by either the surgeon or the robot to continue or cease the surgery.

Figure 2:
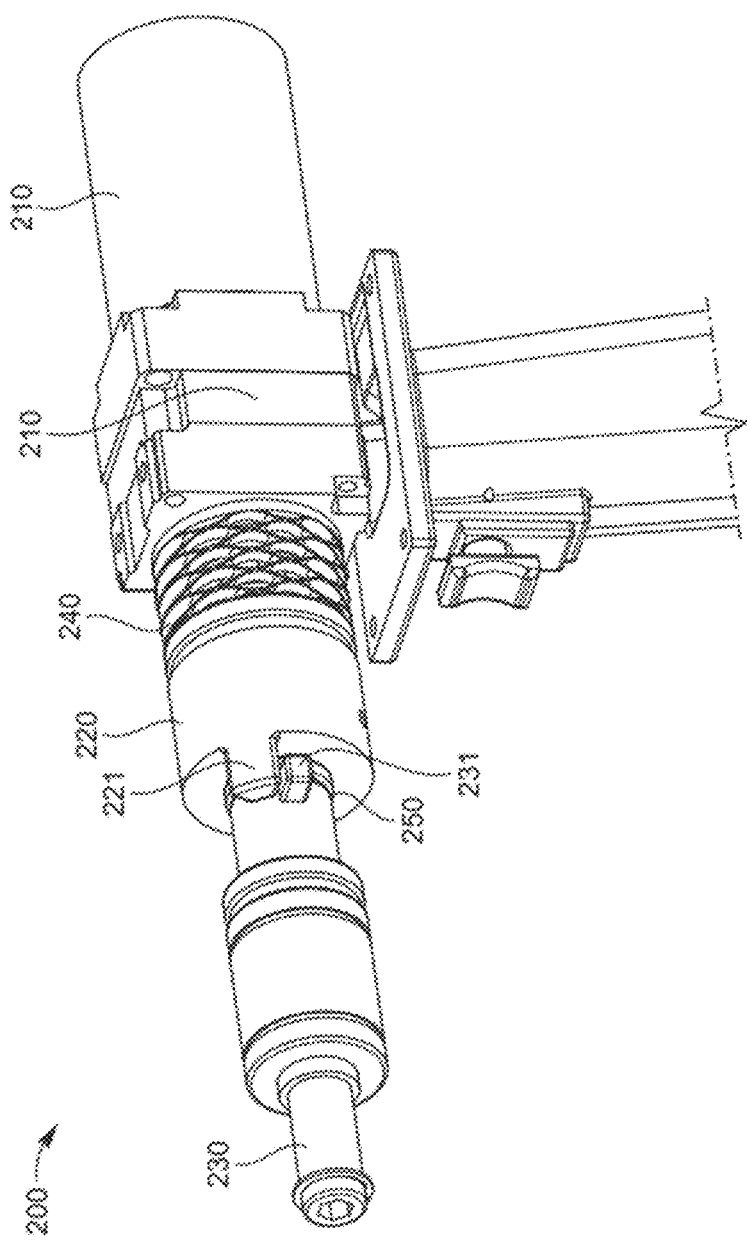
FIG. 2 shows an exemplary hammer and an exemplary output anvil of a torque releasing reaming tool, in accordance with an exemplary embodiment of the present disclosure.

In an embodiment, and as shown in FIG. 1 and FIG. 2, a rotary surgical tool 200 that features rotational movement is shown, which movement allows an intermediary (e.g., a hammer 220) to strike an output anvil 230, which output anvil 230 then may deliver torque to a surgical area, for example. It should be appreciated that the intermediary is configured to be coupled to the input shaft and configured to decouple in response to a torque exerted on a surgical implement exceeding a predetermined torque threshold and recouple upon further rotation of the input shaft as further described herein. In one or more aspects of the disclosed subject matter, the intermediary is the hammer 220. In one aspect, the hammer can be a mass that rotates and impacts the anvil. In an embodiment, the tool 200 comprises a motor and gearbox 210 that is operatively coupled to a leadscrew such as a lead screw element 215. The motor provides for rotational motion of the lead screw element. The lead screw element 215 includes a lead nut 216, which lead nut 216 rotates at substantially the same rpm as the lead screw element 215 and the anvil when the delivered torque to the anvil is below the threshold torque. The hammer 220 is operatively coupled to the lead nut 216 such that the hammer rotates along with the lead nut 216. As the hammer 220 rotates, it may selectively engage and rotate the output anvil 230.

In an embodiment, the hammer 220 comprises at least one tooth or other protrusion 221 that extends longitudinally away from the face 222 of the hammer 220. In an embodiment, the output anvil 230 comprises at least one tooth or other protrusion 231 that extends radially away from the body 232 of the anvil. In an embodiment, the at least one tooth (or protrusion) 221 of the hammer may engage the at least one tooth (or protrusion) 231 of the output anvil 230 such that while the hammer 220 rotates, such engagement causes the output anvil 230 to rotate. The rotation may continue until a sufficiently high torque load is imparted on the output anvil 230, such that the output anvil 230 ceases rotating. This causes the hammer 220 to also stop rotating due to the still-engaged protrusions 231 and 221, respectively of the output anvil 230 and hammer 220.

In an embodiment, the torque release tool 200 further comprises an energy storage component 240 (such as a spring, for example) and a lead screw element (an exemplary example of which is a lead screw element 215). In one or more aspects of the disclose subject matter, the energy storage component as envisioned in the present disclosure is one which can store potential energy using a mechanical method. Examples include but are not limited to gas springs, elastomer springs, mechanical springs, belleville washers and the like. This mechanical potential energy storage does not include energy storage by kinetic energy (e.g., flywheel) although it is understood that the subsequent release of stored potential energy is converted to kinetic energy. In an embodiment, the energy storage component 240 is disposed between the lead nut 216 and the motor 210 of the tool 200. It will be apparent that the coil of the spring facilitates placement of the spring 240 around the lead screw element 215. In an embodiment, the lead screw element is constantly rotating. In such an embodiment, and when the hammer 220 ceases rotation, the lead nut 216 and hammer 220 to which it is attached will translate backwards (away from the output anvil 230). Such backward translation of the lead nut 216 and hammer 220 causes the energy storage component 240 to compress which energizes the energy storage component. The translation and compression continue until the hammer 220 has moved a sufficient backward distance such that the at least one protrusion 221 of the hammer 220 has disengaged (also referred to herein as decoupled) from the at least one protrusion 231 of the output anvil 230.

Once the hammer 220 has moved a sufficient distance backward such that its at least one protrusion 221 has disengaged from the at least one protrusion 231 of the output anvil 230, the hammer teeth face(s) 221a slide along the anvil teeth face(s) until they clear the anvil teeth and the energized energy storage component 240 decompresses to force a high-speed rotational movement of the hammer 220 down the lead screw element 215 toward the output anvil 230. This high-speed rotational movement of the hammer 220 will effect a large increase in the output torque as it re-engages the anvil. In other words, the stored mechanical potential energy (e.g., in the spring) energizes the hammer 220, and the hammer 220 moves to recouple and impart a rotary output torque on the output anvil in excess of the threshold torque. In an embodiment, the motor 210 can be programmed to increase its speed when the hammer 220 is pulling back (which indicates that the threshold torque has been reached and a decoupling event is set to occur). This has the advantage of maintaining a relatively constant anvil and therefore reamer output RPM whether the tool is in the coupling/decoupling stage or the constant rotation stage. It was discovered that this was required in order to limit any potential splatter of bodily fluids caused by an excessively fast output rpm and to prevent an excessively long cutting operation caused by too slow of an output rpm. It is preferable to limit the anvil speed to between 100 and 400 revolutions per minute.

Figure 3:
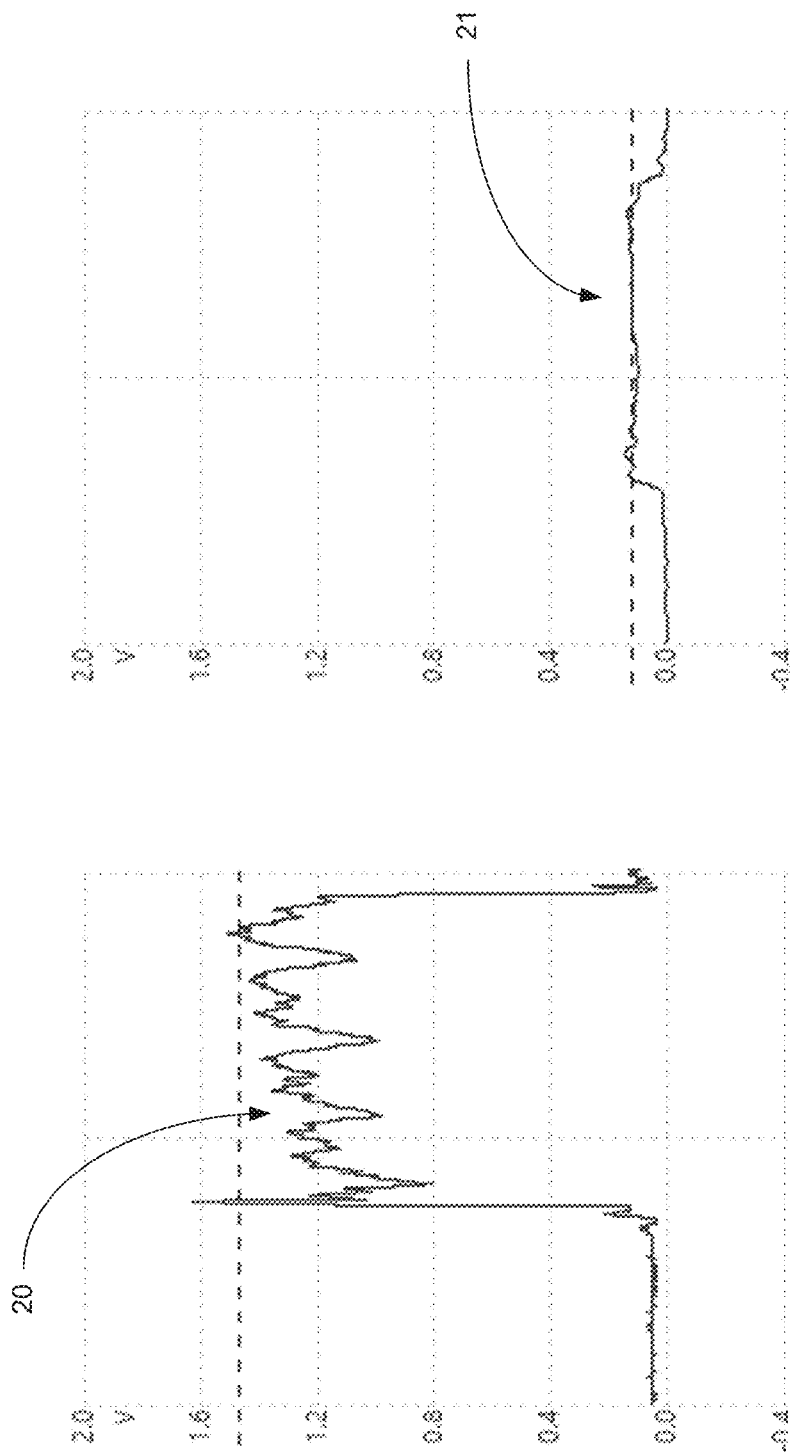
FIG. 3 shows an example graphic comparing reactionary torque of an exemplary embodiment of the present disclosure to a typical surgical reamer.

The torque releasing mechanism described in the present disclosure allows for much higher output torques to be achieved in reaming as compared to conventional orthopedic reaming tools. This improvement is at least 50% and the reactionary torque is less than half that which can be felt with conventional orthopedic reaming tools. It is understood that the improvement of at least 50% is partially a result of the tool operator's ability to handle the present invention in a controllable manner. For example, while an output torque of 150 in-lbs might be attainable with a conventional orthopedic reaming tool, the reactionary torque (also 150 in-lbs) would be so great that the operator's wrist/hand would suffer severe damage if the reaming tool was held onto for a duration longer than 200 ms, A graph where we measured the reactionary torque on both a standard orthopedic reamer and the tool described herein is shown in FIG. 3. The graph was obtained by attaching a torque sensor to the back of a standard orthopedic reamer and attaching the output of the reamer to a known torque load (70 in-lbs). The same procedure was followed with the tool described herein. Curve 20 shows the reactionary torque of a standard orthopedic reamer which fluctuates around 70 in-lbs. Curve 21 shows the reactionary torque of an embodiment of the present disclosure which stays relatively constant at ~6 in-lbs. In an unexpected test, the tool was discovered to switch from the decoupling/recoupling stage to continuous rotary motion stage at or near the completion of the surgical reaming. During the testing we also discovered that the decoupling and recoupling of the anvil results in a noticeable auditory signal which can assist in determining that the surgical operation is nearly completed or fully completed.

When the hammer 220 is forced down the lead screw element 215 due to the decompression of the spring 240, there is linear energy as well as rotary energy available from the hammer 220. The combined linear and rotary energy can be partitioned such that the linear energy can be harnessed to impart an axial movement on the output anvil.

In an embodiment, the tool 200 has the capability to determine the stiffness of the surgical site by measuring the rotational displacement per recoupling event with a sensor. A recoupling event results in a predictable amount of rotational torque to the output anvil 230. As a result, the tool of the present disclosure can be configured to indicate a "staffing" condition. For example, the tool might count 10 recoupling events and determine that the output anvil 230 has only moved by 0.1 degree rotationally over that period of time. The tool may thereupon indicate to the surgeon/ robot (through a status light, sound or a pause or slowing of the tool's operation) that the reamer is no longer advancing and a decision could be made by either the surgeon or the robot to continue or cease the surgery.

In an embodiment, and as seen in FIG. 5A, FIG. 5B, FIG. 5C, and FIG. 6, a rotary axial surgical tool 300 that features rotational movement is shown, which movement allows a hammer 320 to strike an output anvil 330, which output anvil 330 then may deliver torque to a surgical area, for example. In an embodiment, the tool 300 comprises a motor and gearbox 310 that is operatively coupled to a leadscrew such as a lead screw element 315. The motor provides for rotational motion of the lead screw element. The lead screw element 315 includes a lead nut 316, which lead nut 316 rotates at substantially the same rpm as the lead screw element 315 and the anvil when the delivered torque to the anvil is below the threshold torque. The hammer 320 is operatively coupled to the lead nut 316 such that the hammer rotates along with the lead nut 316. As the hammer 320 rotates, it may selectively engage and rotate the output anvil 330.

In an embodiment, the hammer 320 comprises at least one tooth or other protrusion 321 that extends longitudinally away from a face 322 of the hammer 320. In an embodiment, the output anvil 330 comprises at least one ear or other protrusion 331 that extends radially away from the body 332 of the anvil. In an embodiment, the at least one tooth (or protrusion) 321 of the hammer may engage the at least one ear (or protrusion) 331 of the output anvil 330 such that while the hammer 320 rotates, such engagement causes the output anvil 330 to rotate. The rotation may continue until a sufficiently high torque load is imparted on the output anvil 330, such that the output anvil 330 ceases rotating. This causes the hammer 320 to also stop rotating due to the still-engaged protrusions 331 and 321, respectively of the output anvil 330 and hammer 320.

In an embodiment, the torque release tool 300 further comprises an energy storage component 340 (such as a spring, for example) and a lead screw element (an exemplary example of which is a lead screw element 315). In an embodiment, the energy storage component 340 is disposed between the lead nut 316 and the motor 310 of the tool 300. The coil of the spring facilitates placement of the spring 340 around the lead screw element 315. In an embodiment, the lead screw element is constantly rotating. In such an embodiment, and when the hammer 320 ceases rotation, the lead nut 316 and hammer 320 to which it is attached will translate backwards (away from the output anvil 330). Such backward translation of the lead nut 316 and hammer 320 causes the energy storage component 340 to compress which energizes the energy storage component. The translation and compression continue until the hammer 320 has moved a sufficient backward distance such that the at least one protrusion 321 of the hammer 320 has disengaged (also referred to herein as decoupled) from the at least one protrusion 331 of the output anvil 330.

Once the hammer 320 has moved a sufficient distance backward such that its at least one protrusion 321 has disengaged from the at least one protrusion 331 of the output anvil 330, the hammer teeth face(s) slide along the anvil protrusion face(s) until they clear the anvil ears and the energized energy storage component 340 decompresses to force a high-speed rotational movement of the hammer 320 down the lead screw element 315 toward the output anvil 330. This high-speed rotational movement of the hammer 320 will effect a large increase in the output torque as it re-engages the anvil. In an embodiment, the motor 310 can be programmed to increase its speed when the hammer 320 is pulling back (which indicates that the threshold torque has been reached and a decoupling event is set to occur). This has the advantage of maintaining a relatively constant anvil and therefore reamer output RPM whether the tool is in the coupling/decoupling stage or the constant rotation stage. It was discovered that this speed control was required in order to limit any potential splatter of bodily fluids caused by an excessively fast output rpm and to prevent an excessively long cutting operation caused by too slow of an output rpm. It is preferable to limit the anvil speed to between 100 and 400 revolutions per minute.

Figure 6:
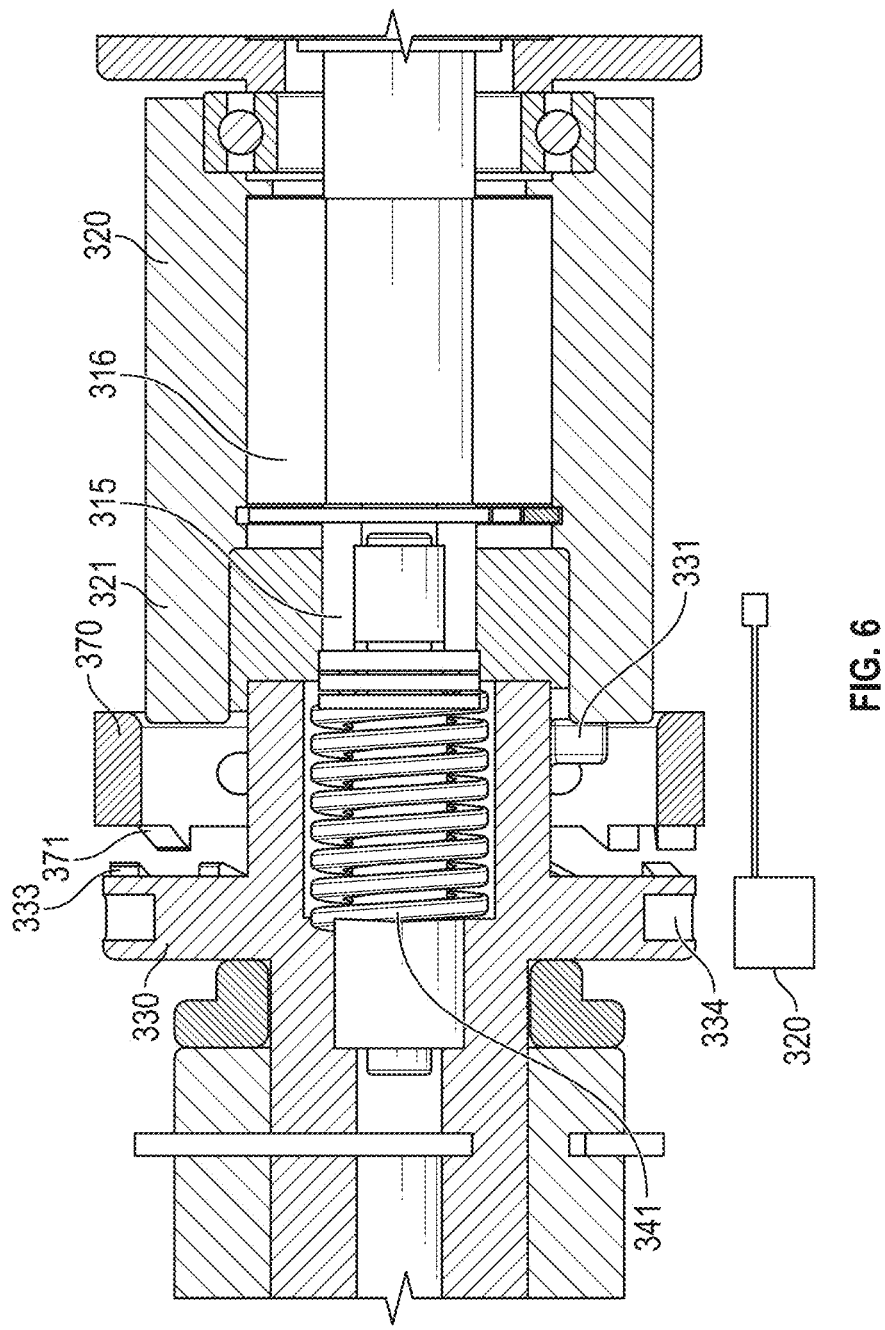
FIG. 6 shows a cross section view of a rotary reaming tool with an optional axial displacement in accordance with an exemplary embodiment of the present disclosure.
Figure 7A:
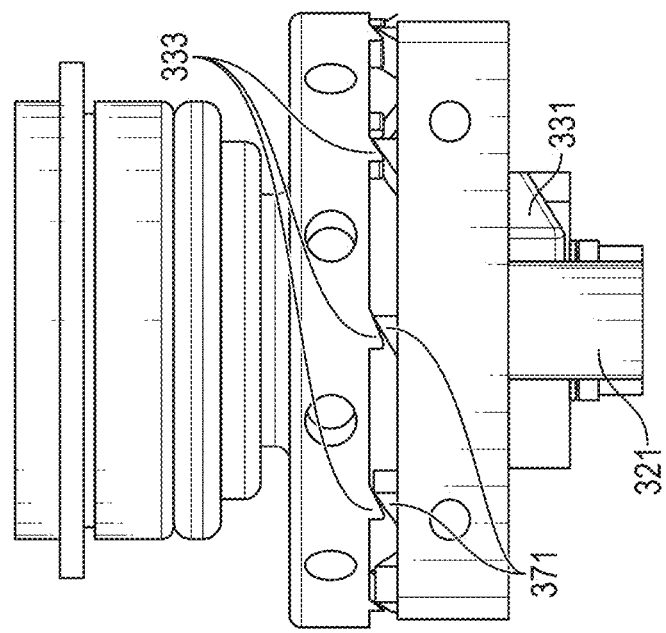
FIG. 7A shows a cross section view of a rotary axial reaming tool wherein the linear actuator spring is uncompressed.
Figure 7B:
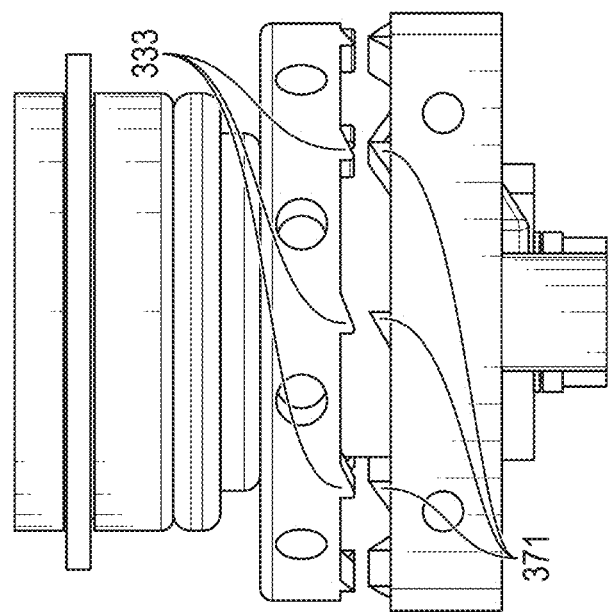

Rotary axial surgical tool 300 has the capability to selectively effect axial movement upon the surgical implement. Referring to FIG. 6, the rotary axial surgical tool 300 comprises a linear actuator spring 341, which operates to selectively engage axial contact events. An axial contact event occurs when the protrusions 333 of output anvil 330 engage with the protrusions 371 of the linear hammer 370. Axial contact events occur when the output anvil 330 is being rotated by the hammer 320 and the linear actuator spring 341 is compressed at or above a linear threshold force. The linear actuator spring 341 is compressed when the tool operator pushes the surgical implement axially into the surgical site. This method of engaging axial movement of the output anvil is illustrated by looking at FIG. 7A and FIG. 7B. FIG. 7A shows the interaction between the rotating output anvil protrusions 333 and the fixed linear hammer protrusions 371 when the operator is pushing into the surgical site with a force less than linear threshold force. FIG. 7B shows the interaction between the output anvil protrusions 333 and the fixed linear hammer protrusions 371 when the operator is pushing into the surgical site with a force greater than the linear threshold force. For example, in response to the linear force imparted on the rotary tool by the surgeon or robot exceeding the threshold linear force, the output anvil moves axially. In one aspect, the threshold linear force is at least 4 lbs and the axial stroke is less than 2 mm.

Figure 9:
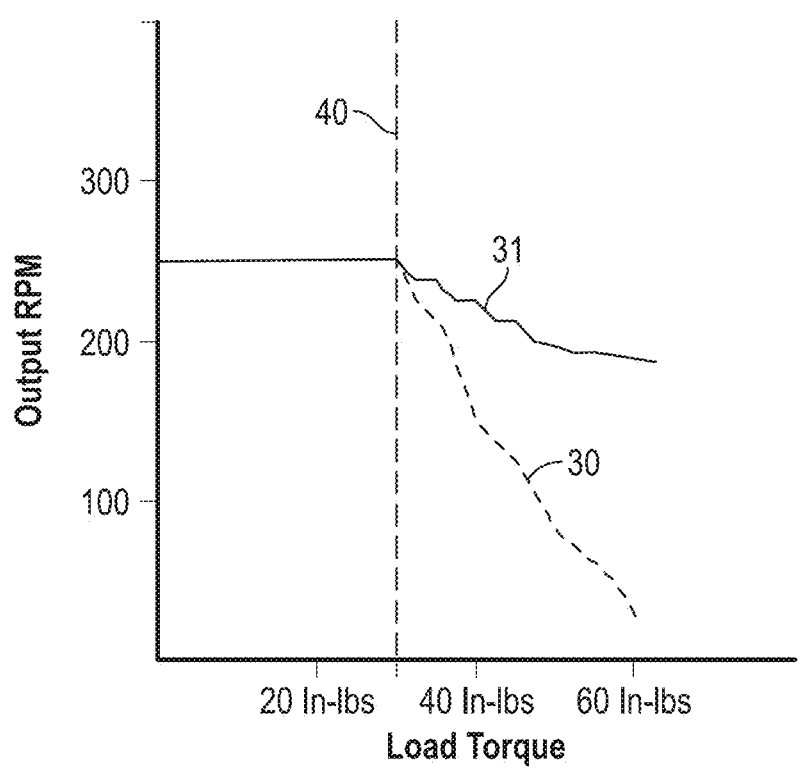
FIG. 9 shows an example graph of output RPM versus load torque for a reactionary torque decoupling reaming tool with output RPM tracking sensor compared to a reactionary torque decoupling reaming tool without output RPM tracking sensor.

It is valuable to maintain a stable output rpm in the range of 100 to 400 rpm at the anvil and corresponding attached surgical implement. In an embodiment, a sensor such as a hall sensor 350 can be used to detect angular position of the output anvil. In an embodiment where the sensor is a hall sensor, the output anvil can comprise at least one magnet and more preferably a plurality of magnets 334 which encircle the output anvil. The magnets are detected by the hall sensor which can be used to indicate angular position of the output anvil and/or rotational speed of the output anvil. This can be used in conjunction with a controller to adjust the motor speed in response to the various load and/or decoupling and recoupling events to maintain an appropriate anvil speed. In one aspect, the controller can include or be encompassed by circuitry. Circuitry as used in the present application can be defined as one or more of the following: an electronic component (such as a semiconductor device), multiple electronic components that are directly connected to one another, or interconnected via electronic communications, a computer, a network of computer devices, a remote computer, a web server, a cloud storage server, and/or a computer server. For example, each of the one or more of the computer, the remote computer, the web server, the cloud storage server, and the computer server can be encompassed by or may include the circuitry as a component(s) thereof. In some embodiments, multiple instances of one or more of these components may be employed, wherein each of the multiple instances of the one or more of these components are also encompassed by or include circuitry. In some embodiments, the circuitry represented by the networked system may include a serverless computing system corresponding to a virtualized set of hardware resources. The circuitry represented by the computer may be a personal computer (PC), a desktop computer, a laptop computer, a tablet computer, a netbook computer, a personal digital assistant (PDA), a smart phone, or any other programmable electronic device capable of communicating with other devices on the network. The circuitry may be a general-purpose computer, special purpose computer, or other programmable apparatus as described herein that includes one or more processors. Each processor may be one or more single or multi-chip microprocessors. Processors are considered processing circuitry or circuitry as they include transistors and other circuitry therein. The circuitry may implement the systems and methods described in this disclosure based on computer-readable program instructions provided to the one or more processors (and/or one or more cores within a processor) of one or more of the general purpose computer, special purpose computer, or other programmable apparatus described herein to produce a machine, such that the instructions, which execute via the one or more processors of the programmable apparatus that is encompassed by or includes the circuitry, create a system for implementing the functions specified in the present disclosure. Alternatively, the circuitry may be a preprogrammed structure, such as a programmable logic device, application specific integrated circuit, or the like, and is/are considered circuitry regardless if used in isolation or in combination with other circuitry that is programmable, or preprogrammed. Referring to FIG. 9, curve 30 shows a graph of the average output RPM for a decoupling/recoupling rotary tool with uncontrolled output RPM at various load torques. Curve 31 shows a graph of the average output RPM for a decoupling/recoupling rotary tool with active RPM control at various load torques. The dotted line 40 illustrates a typical threshold torque (i.e. the load torque at which decoupling/recoupling starts to occur). A load torque above the threshold torque value for an uncontrolled output RPM rotary tool results in a much slower RPM compared to a rotary tool with an actively controlled output RPM. It should be understood, that the RPM of a surgical implement is directly related to advancement rate (i.e. a slower RPM results in a slower reaming process because the cutting edges of the surgical implement are moving slower). It is therefore advantageous to control the output RPM to stay within a range of 100 to 400 RPM.

The present disclosure offers various advantages including; reduction of reactionary forces from a surgical tool to the gripping and or mounting surface. Another advantage is that the tool will provide a significant amount of the forces required to complete a surgery without the need for external forces (for example, the external supporting force from a surgeon that leans into the reamer handpiece to get the reamer to advance axially in the surgical site). This results in less wear and tear on a robotic platform in the case of robotic surgery and less surgeon fatigue for a surgeon operator. This also improves the accuracy and capability of the robot in the case of a robotic surgical tool and may drastically reduce instances of a loss of registration by a surgical robot.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the disclosure and various embodiments with various modifications as are suited to the particular use contemplated,

What is claimed is:

1. A rotary tool for orthopedic surgery, the rotary tool comprising:
    a motor coupled to an input shaft;
    an intermediary coupled to the input shaft;
    an output anvil;
    a surgical implement coupled to the output anvil;
    wherein in response to a torque exerted on the surgical implement exceeding a threshold torque, the intermediary decouples from the output anvil, and
    upon further rotation of the input shaft, the intermediary moves to recouple and impart a rotary output torque on the output anvil in excess of the threshold torque.

2. The rotary tool of claim 1, wherein the intermediary is energized to move to recouple by stored mechanical potential energy, wherein the stored mechanical potential energy is stored by a mechanical spring or a gas spring.

3. The rotary tool of claim 1, wherein the threshold torque is less than 35 inch-pounds.

4. The rotary tool of claim 1, wherein the recoupling of the intermediary to the output anvil increases the output torque by more than 50% of the threshold torque.

5. The rotary tool of claim 1, wherein the transition between the coupling and decoupling of the intermediary to the output anvil includes one or more of an audible and visible signal.

6. The rotary tool of claim 1, further comprising:
    at least one sensor, wherein the rotary tool position is determined only when the output torque is less than the threshold torque.

7. The rotary tool of claim 1, further comprising:
    a controller configured to adjust the speed of the motor to maintain an output RPM of the anvil within a range of 100 to 400 rpm.

8. A rotary tool for orthopedic surgery, the rotary tool comprising:
    a motor coupled to an input shaft;
    an intermediary coupled to the input shaft;
    an output anvil;
    a surgical implement coupled to the output anvil;
    wherein in response to a torque exerted on the surgical implement exceeding a threshold torque, the intermediary decouples from the output anvil, and
    upon further rotation of the input shaft, the intermediary moves to recouple and impart a rotary output torque on the output anvil in excess of the threshold torque,
    wherein in response to the linear force imparted on the rotary tool by the surgeon or robot exceeding a threshold linear force, the output anvil moves axially.

9. The rotary tool of claim 8, wherein the intermediary is energized to move to recouple by stored mechanical potential energy, wherein the stored mechanical potential energy is stored by a mechanical spring or a gas spring.

10. The rotary tool of claim 8, wherein the threshold torque is less than 30 inch-pounds.

11. The rotary tool of claim 8, wherein the recoupling of the intermediary to the output anvil increases the output torque by more than 50% of the threshold torque.

12. The rotary tool of claim 8, wherein the transition between the coupling and decoupling of the intermediary to the output anvil includes one or more of an audible and visible signal.

13. The rotary tool of claim 8, further comprising:
    a sensor which sensor causes the tool to shut off, slow down, emit light, or otherwise provide a cue in response to the forward progress of the surgical implement is less than 0.01 mm in 1 second.

14. The rotary tool of claim 8, wherein the threshold linear force is at least 4 lbs and the axial stroke is less than 2 mm.

15. The rotary tool of claim 8, further comprising:
    a controller configured to adjust the speed of the motor to maintain an output RPM of the anvil within a range of 100 to 400 rpm.

16. A rotary tool for orthopedic surgery, the rotary tool comprising:
    a motor coupled to an input shaft;
    an intermediary coupled to the input shaft;

a mechanical potential energy storage coupled to the intermediary;

an output anvil;

a surgical implement coupled to the output anvil;

wherein in response to a torque exerted on the surgical implement exceeding a threshold torque, the intermediary decouples from the output anvil and mechanical potential energy is increased in the mechanical potential energy storage through rotation of the input shaft, and upon further rotation of the input shaft, the intermediary is energized by the stored mechanical potential energy and thereafter moves to recouple and impart a rotary output torque on the output anvil in excess of the threshold torque.

17. The rotary tool of claim 16, wherein the mechanical potential energy storage is a mechanical spring or a gas spring.

18. The rotary tool of claim 16, wherein the intermediary is a hammer.

19. The rotary tool of claim 16, wherein the threshold torque is less than 30 inch pounds.

20. The rotary tool of claim 16, wherein the recouping of the hammer to the output anvil gives an increase in output torque of more than 50% of the threshold torque.

* * * * *